United States Patent [19]
Choi

[11] Patent Number: 5,343,746
[45] Date of Patent: Sep. 6, 1994

[54] HUMIDITY SENSING APPARATUS

[75] Inventor: Jin K. Choi, Suweon, Rep. of Korea

[73] Assignee: Samsung Electronics Co., Ltd., Suwon, Rep. of Korea

[21] Appl. No.: 20,714

[22] Filed: Feb. 22, 1993

[30] Foreign Application Priority Data

Feb. 20, 1992 [KR] Rep. of Korea .................. 92-2485

[51] Int. Cl.$^5$ ........................................... G01N 25/56
[52] U.S. Cl. .................................................. 73/335.05
[58] Field of Search .................................... 73/335.05

[56] References Cited

U.S. PATENT DOCUMENTS

| | | | |
|---|---|---|---|
| 3,196,682 | 7/1965 | Johnson, Jr. ...................... | 73/335.05 |
| 4,335,293 | 6/1982 | Kobayashi et al. ........... | 73/335.05 X |
| 4,546,916 | 10/1985 | Tsuaki ........................ | 73/335.05 X |
| 4,768,378 | 9/1988 | Ando et al. ...................... | 73/335.05 |
| 5,040,417 | 8/1991 | Rowlette ........................ | 73/335.05 |

FOREIGN PATENT DOCUMENTS

58-181288  10/1983  Japan .

*Primary Examiner*—Hezron E. Williams
*Assistant Examiner*—Joseph W. Roskos
*Attorney, Agent, or Firm*—Burns, Doane, Swecker & Mathis

[57] ABSTRACT

A humidity sensing apparatus is operated by an AC power supply. The humidity sensing apparatus comprises a humidity sensing section including a humidity sensor and a divider resistor connected in parallel to the humidity sensor; a humidity sensor operating section for supplying the humidity sensor with an AC voltage within predetermined voltage levels; and, a humidity signal converting section including diodes, condensers and resistors. The humidity signal converting section converts the AC humidity signal output from the humidity sensing section into a corresponding DC humidity signal by selecting the time constants of the pair of condenser-resistor circuits and then supplies the peripheral digital circuits with the converted signals.

5 Claims, 2 Drawing Sheets

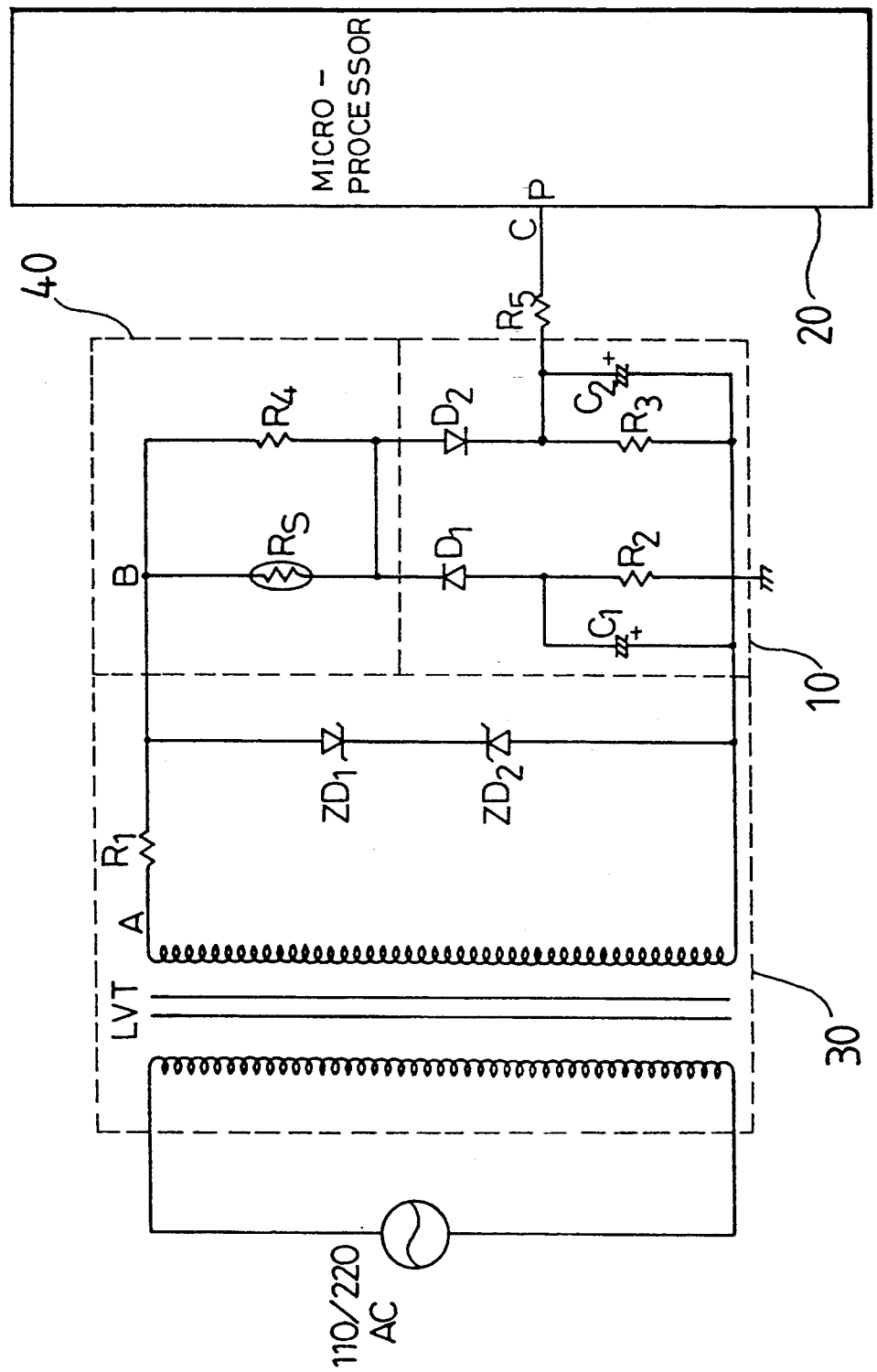

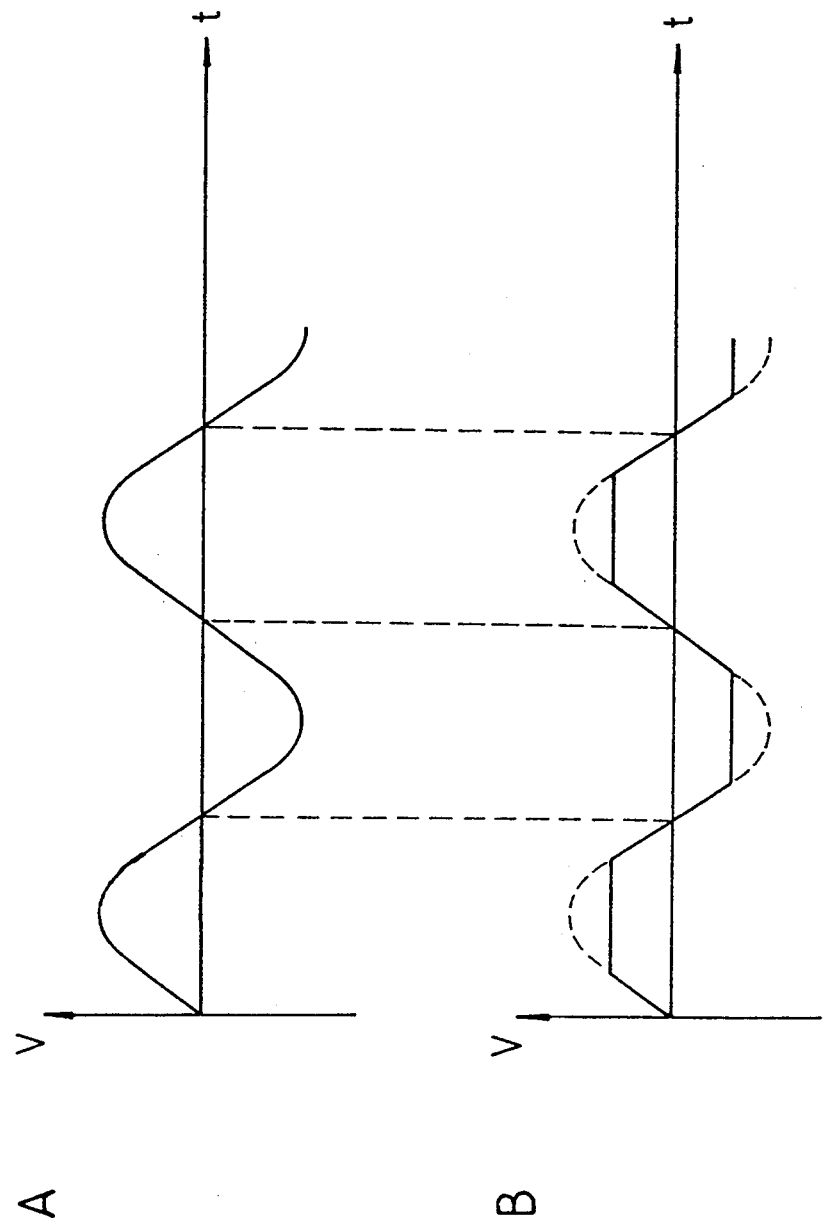

HUMIDITY SENSING APPARATUS

FIELD OF THE INVENTION

The present invention is related to a humidity sensing apparatus for sensing humidity in the interior of a cooking chamber of a food heating appliance such as a microwave oven.

BACKGROUND OF THE INVENTION

A humidity sensor, currently used in various fields, is used in a microwave oven which heats and cooks foods by utilizing the principle of dielectric heating, to increase the cooking efficiency. Automatic cooking may be enhanced by monitoring the humidity in the cooking chamber using a humidity sensor. Conventional art using such a humidity sensor is disclosed in Japanese Patent Laid-Open No. 181288 (1983). When a comparator compares a voltage signal from the humidity sensor with a reference voltage which is produced by a microprocessor and converted through a reference voltage generator, the resolution of the reference voltage or the response speed can be varied by increasing and/or decreasing the number of bits from the microprocessor according to kinds of food to be cooked. The conventional apparatus applies constant DC voltage to the branch of a humidity sensor and a fixed resistor connected in series, and then determines whether to complete the cooking process by comparing the voltage at the junction of the humidity sensor and the fixed resistor with the reference voltage. The humidity sensor is operated with a constant DC voltage so that an additional rectifier circuit is not needed and the interface with peripheral digital circuits is simplified. However, when constant DC voltage is applied to the humidity sensor for a long time, the sensing efficiency of the humidity sensor decreases.

SUMMARY OF THE INVENTION

It is an object of the present invention to provide a humidity sensing apparatus with a simple configuration.

It is another object of the present invention to provide a humidity sensing apparatus which is driven by an AC power source, thereby improving the sensing efficiency of a humidity sensor.

It is still another object of the present invention to provide a humidity sensing apparatus capable of interfacing with peripheral digital circuits without additional analog to digital converting circuits.

A humidity sensing apparatus of the present invention comprises a humidity sensing section including a humidity sensor and a divider resistor connected in parallel to the humidity sensor; a humidity sensor operating section for supplying the humidity sensor with an AC voltage within predetermined voltage levels; and, a humidity signal converting section for converting the AC humidity signal output from the humidity sensing section into a corresponding DC humidity signal.

BRIEF DESCRIPTION OF THE DRAWINGS

The foregoing objects and advantages may be more fully understood by reading the description of the preferred embodiment with reference to the accompanying drawings wherein:

FIG. 1 is a circuit diagram of a humidity sensing apparatus according to the present invention;

FIGS. 2A and 2B are waveform diagrams of an input AC power supply and voltage applied to a humidity sensor, respectively.

DETAILED DESCRIPTION OF THE PREFERRED EMBODIMENT

FIG. 1 is a circuit diagram of a humidity sensing apparatus according to the present invention. The humidity sensing apparatus comprises a humidity sensing section 40, a humidity sensor operating section 30, a humidity signal converting section 10. A microprocessor 20 controls the entire operation of the appliance which is for example, a microwave oven. The humidity sensing section 40 includes a humidity sensor Rs and a divider resistor R4 connected in parallel to the humidity sensor Rs. The humidity sensor operating section 30 includes a low voltage transformer LVT for stepping down the input AC power supply, a pair of Zener diodes ZD1 and ZD2 having anodes connected between two terminals of the secondary winding of the transformer LVT and cathodes connected to each other, and a divider resistor R1 inserted in series between one terminal of the secondary winding of the transformer LVT and the anode of the Zener diode ZD1. The humidity sensor Rs and the divider resistor R4 are also connected in parallel to the anode of the Zener diode ZD1. The humidity signal converting section 10 includes two diodes D1 and D2 for setting the current direction, condensers C1 and C2 and resistors R2 and R3 for charging and discharging. The cathode of the diode D1 and the anode of the diode D2 are connected in parallel to the other junction of the humidity sensor Rs and the resistor R4. The condenser C1 and the resistor R2 are connected in parallel to the anode of the diode D1, and the condenser C2 and the resistor R3 are connected in parallel to the cathode of the diode D2. All other terminals of the condensers C1 and C2 and the resistors R2 and R3 are grounded. Moreover, the junction of the diode D2, condenser C2 and resistor R3 is connected to a corresponding input port P of the microprocessor 20 via a current limiting resistor R5.

The operation of the humidity sensing apparatus will now be described. FIGS. 2A and 2B are waveform diagrams of the input AC power supply and the voltage applied to the humidity sensor, respectively. Initially, a commercial AC power supply with the waveform as shown in FIG. 2A is stepped down through the transformer LVT, and converted by the divider resistor R1 and the Zener diodes ZD1 and ZD2 into a voltage waveform with predetermined clipped levels as shown in FIG. 2B. Next, the clipped voltage is supplied to the humidity sensing section 40, which is designed to increase the sensing efficiency of the humidity sensor Rs. Next, AC current passes through the humidity sensor Rs and the resistor R4 as appropriately divided according to the humidity level at the location where the humidity is detected. During the positive half of the cycle in FIG. 2B, the diode D2 is in the ON state and the diode D1 is in the OFF state. Accordingly, the condenser C2 charges and the condenser C1 discharges through the resistor R2. During the negative half of the cycle, the operation of the diodes D1 and D2 and the condensers C1 and C2 are reversed from the operation during the positive half of the voltage cycle. Accordingly, if the an time constants of R2*C1 and R3*C2 are appropriately selected, a DC humidity signal proportional to an AC humidity signal sensed through the humidity sensor Rs is obtained at the port P of the microprocessor 20. Moreover, if the parameter values of diode D1, condenser C1 and resistor R2 are the same as those of diode D2, condenser C2 and resistor R3, respectively, the sensing efficiency of the humidity sensor can be further increased.

We claim:

1. A humidity sensing apparatus, comprising:

means for supplying a predetermined AC voltage, said means including a first AC output terminal and a second AC output terminal;

a humidity sensor connected between a first humidity sensor terminal and a second humidity sensor terminal, said first humidity sensor terminal being connected to said first AC output terminal;

a first diode, a cathode of said first diode being connected to said second humidity sensor terminal;

a first charging/discharging means connected between an anode of said first diode and said second AC output terminal;

a second diode, an anode of said second diode being connected to said second humidity sensor terminal;

a second charging/discharging means connected between a cathode of said second diode and said second AC output terminal; and means connected to said cathode of said second diode for calculating a humidity level based on a current signal passing through said second diode.

2. The humidity sensing apparatus of claim 1 wherein said supplying means includes, a low-voltage transformer for stepping down an input AC power supply, a divider resistor wherein a first terminal thereof is connected in series to a first terminal of a secondary winding of said transformer, and a pair of zener diodes, each zener diode having an anode connected between a second terminal of said divider resistor and a second terminal of said secondary winding, a cathode of each zener diode being connected to a cathode of the other, each of said first AC output terminal and said second AC output terminal being respectively connected to an anode of a respective one of said pair of zener diodes.

3. Apparatus as claimed in claim 1, wherein said first charging/discharging means comprises:

a resistor connected between said anode of said first diode and ground; and a capacitor connected between said anode of said first diode and said second AC output terminal.

4. Apparatus as claimed in claim 1, wherein said second charging/discharging means comprises:

a resistor connected between said cathode of said second diode and said second AC output terminal; and a capacitor connected between said cathode of said second diode and said second AC output terminal.

5. Apparatus as claimed in claim 1, wherein said means connected to said cathode of said second diode for calculating a humidity level based on a current signal passing through said second diode comprises:

a current limiting resistor connected to said cathode of said second diode; and a microprocessor connected to said cathode of said second diode through said current limiting resistor.

* * * * *